United States Patent [19]
Roberts

[11] Patent Number: 4,812,447
[45] Date of Patent: Mar. 14, 1989

[54] METHOD FOR THE TREATMENT OF NERVOUS SYSTEM DEGENERATION

[75] Inventor: Eugene Roberts, Monrovia, Calif.

[73] Assignee: City of Hope, Duarte, Calif.

[21] Appl. No.: 940,789

[22] Filed: Dec. 11, 1986

Related U.S. Application Data

[63] Continuation of Ser. No. 790,080, Oct. 22, 1985, abandoned.

[51] Int. Cl.$^4$ ............... A61K 31/55; A61K 31/56
[52] U.S. Cl. ............... 514/170; 514/213; 514/866
[58] Field of Search ............... 514/170, 213, 866

[56] References Cited

U.S. PATENT DOCUMENTS 4,507,289  3/1985  Coleman et al. ............... 514/170

*Primary Examiner*—Stanley J. Friedman
*Attorney, Agent, or Firm*—Edward S. Irons

[57] ABSTRACT

Disclosed is a method for treating nervous system deterioration associated with aging and Alzheimer's disease by administering a therapeutically-effective amount of dehydroepiandrosterone or its sulfate. Also disclosed is the co-administration of dehydroepiandrosterone or its sulfate and a potassium channel antagonist. The disclosure is also directed to pharmaceutical compositions containing dehydroepiandrosterone, alone or in combination with a potassium channel antagonist. Dehydroepiandrosterone is also shown to facilitate the growth of nervous system tissue, particularly in culture.

6 Claims, No Drawings

METHOD FOR THE TREATMENT OF NERVOUS SYSTEM DEGENERATION

CROSS-REFERENCE TO RELATED APPLICATONS

This is a continuation of application Ser. No. 790,080 filed Oct. 22, 1985, now abandoned.

BACKGROUND OF THE INVENTION

This invention relates to the treatment of degenerative diseases of the central nervous system, such as those associated with aging and senile dementia of the Alzheimer's type (hereinafter referred to by the abbreviation SDAT). In particular, this invention also relates to methods for preparing pharmaceuticals useful in the treatment of nervous system degeneration, pharmaceutical compositions useful for said treatment and to methods for facilitating the growth and repair of damaged nerve tissue, including brain cells.

SDAT, commonly called Alzheimer's disease, is a progressive degenerative disorder of the central nervous system leading to severe disturbances in perception, memory, and overall neurological function. In advanced cases, gross pathological alterations in the structure of the brain itself are visible. A large body of current research is directed toward elucidating the causes and mechanisms of this disease and toward halting or reversing its debilitating progress.

The sex hormones, the androgens and estrogens, are known to counter various non-neurological symptoms of aging. However, problems typically arise that preclude prolonged use of the hormones. These problems include endometrial bleeding, prostatic hypertrophy, and signs of carcinogenesis.

One precursor of the androgens and estrogens, dehydroepiandrosterone (hereinafter referred to by the abbreviation DHEA) or its sulfate (hereinafter referred to by the abbreviation DHEAS) has been shown to have a number of therapeutic effects. Serum levels of DHEA decrease over the life span of a human being. It has been shown, for example, that administration of DHEA or DHEAS can reduce the incidence of breast cancer in mice, can reduce obesity in such mice, and that after prolonged administration of DHEA, the mice that have received the compound appear to be younger than mice that have not. Science News 119, 39 (Jan. 17, 1981). This has led to speculation that DHEA compounds may retard the aging process. See also A. Rosenfeld, Omni 59 et seq. (August, 1982) and A. Rosenfeld, Science 81 2, 20–21 (November, 1981). The use of DHEA compounds to treat diabetes has been reported. See, e.g., U.S. Pat. Nos. 4,507,289 and 4,518,595. DHEA has also been used in topical applications for preventing dry skin. U.S. Pat. No. 4,496,558. However, the action of DHEA and related compounds on the nervous system of mammals has been substantially unexplored.

Current research indicates that the symptoms of SDAT reflect the inability of the organism to continue to compensate for continuing degenerative changes in the biochemical machinery of the organism and the cell. Ideally, a living organism and its parts are cybernetic: the various elements effectively communicate with and respond to each other and to the environment in an adaptive way to maintain an ideal, steady-state condition.

Manifestations of aging of the nervous system—whether one looks at neuropathologic, physiologic, neurochemical or behavioral aspects—appear to reflect a final common path taken by organisms when behavioral options ordinarily available to achieve adaptive responses are precluded by degeneration of the neural machinery. Even during the early "normal" adult period, degenerative changes probably are taking place to some extent, but are being compensated for by activities of redundant neural elements and by adjustments in neural feedback and modulator systems. However, eventually pathologic changes may become sufficiently extensive so that the latter activities are inadequate and the social behavior and physiological responses of the severely affected individual become maladaptive and, in the case of humans, survival becomes dependent upon extensive use of artificial social and medical support systems. The endstage pathologies observed are characterized by degenerative changes in cells in many brain regions and are associated with losses of neuronal cells, decreases in neuronal processes in surviving cells, and increases in glial elements. Viral and bacterial infections, dietary deficiencies and imbalances, cardiovascular, metabolic, and endocrine disorders, anoxia, various types of space occupying lesions and traumata, and toxins, may, by themselves, cause degenerative changes or they may predispose to such changes in response to subsequent cerebral insult or injury. Accelerated degeneration of neural, endothelial, neuroendocrine, and endocrine elements together with incoordination in the networks of relations among the cellular components of the immune system, and coincident disruption of neurovascular relations and breakdown of the blood brain barrier in the affected regions, could predispose to the developement of both circulating and cellular autoantibodies to various cellular and extracellular components in the disrupted regions. This may lead to enhanced cellular destruction and deposition of the relatively indigestible debris of immune complexes in capillaries and extracellular sites. Another consequence of perturbation of the immune system might be immunosuppression with resultant activation of latent viruses destructive to the nervous system.

Cells, like organisms, are integrated organizations of a highly heterogeneous nature. They contain thousands of different chemical substances of varying degrees of complexity in physical and chemical interactions with each other in various subcellular organelles and compartments, many of which are morphologically distinguishable by light or electron microscopy. The structures of cell membranes and of membranes of the intracellular organelles have varying stabilities. The membranes have differing degrees of exchangeability with their immediate environment, and the enzyme systems associated with them catalyze some of the chemical reactions by which the internal needs of the individual cells are subserved as well as by which the relations with the extracellular environment are maintained.

When ligands attach to their specific receptors on particular membranes, cascades of biochemical reactions are set in motion in a coordinated way so that in a brief period the cells of which they are a part react appropriately in a manner compatible with their individual behavioral repertoire. Any havoc wrought by the messages the ligands bring is repaired, and the cellular machinery may be altered in such a way as to integrate the messages that the ligands bring. Manifestations of aging—pathologic, physiologic, or biochemical—appear to reflect a common path taken by cells when the mechanisms ordinarily available to achieve adaptive responses, such as those alluded to above, are precluded by degenerative changes in the cellular machinery. Degenerative changes always must be taking place to some extent in any given cell, but are being compensated for by redundant cellular elements and by cybernetic adjustments among the varieties of degradative and synthetic mechanisms. As in the case of the whole organism, when this is no longer possible, aging is said to take place and cell death eventually occurs.

It may be concluded that aging phenomena, at all levels from social to molecular, result in decyberneticization, i.e., disruption of meaningful communication channels between components of relevant members of interlocking systems, so that eventually overtly observable adaptive behaviors are not possible and the organism can no longer function or survive.

Because SDAT of the sporadic type almost always occurs coextensively with aging, many pathological features of decyberneticization are shared. However, SDAT should not be considered entirely in the same category as normal attritional types of aging because, in addition to the above general types of aging changes, important genetic components exist in familial SDAT (there are pedigrees showing what appears to be an autosomal dominant transmission of the disorder) and idiosyncratic reactions to ubiquitously present environmental factors also may play an important role. Behavioral, pathologic, and biochemical data are consistent with the hypothesis that in SDAT the degenerative changes observed in several brain regions are correlated with initial malfunction and subsequent degeneration of terminals of neurons whose somata lie in regions of the brainstem core and whose fibers project to many structures both above and below their location. In SDAT there often is a specific loss of neurons in the basal nucleus of Meynert (Whitehouse, et al., *Ann. Neural.* 10, 122 (1981)) and sometimes in the locus oceruleus (Bondareff, et al., *Neurology* 32, 164 (1982)), which are the major sources of extrinsic cholinergic and noradrenergic inputs, respectively, projecting widely and diffusely upon all telencephalic structures. There is evidence that the hippocampus, a region of the brain known to play a key role in memory formation, essentially may be removed from brain circuitry by lesions at its input and output sites (Hyman, et al., *Science* 225, 1168 (1984)).

Both in SDAT and in "normal" aging, changes in membranes of capillary endothelial cells may influence the rate of entry of substances into the central nervous system by diffusion, pinocytosis, or carrier-mediated transport; or the rate of pumping of $K^+$ ions out of the brain extracellular compartment may be changed. Indeed, it has been suggested from detailed electron microscopic observations that capillary degeneration with the formation of amyloid fibrils may be the primary change in the genesis of senile plaques of SDAT (Miyakawa, et al, *Virchows Arch. [Cell Pathol.]* 40, 121 (1982)). Effects on neural membranes may produce decreases in their conductile properties, changes in release characteristics from terminals of neurotransmitters and modulators, alterations in the sensitivity of pre- and postsynaptic receptors to the action of the latter, and changes in degrees of electrotonic communication between neurons via gap junctions. At the onset of the disease, a whole host of cybernetic adjustments would be expected to be taking place, structural and enzymatic, so that metabolic steady states different from those found before would exist at cellular and tissue levels, and new transactional states would be found at the systems level in the CNS. This process may continue as the disease progresses, until breakdowns occur in one or another rate-limiting process, leading to progressive deterioration and finally fatal loss of adaptive function.

Thus, if the rate-limiting steps or events in an organism's adaptive and compensatory response to biological and biochemical changes associated with SDAT can be identified, one may treat the symptoms and arrest the degenerative progress of the disease by removing the rate-limiting factors.

SUMMARY OF THE INVENTION

According to the invention there is provided a method for promoting the growth of nervous system tissue which comprises treating that tissue with at least one dehydroepiandrosterone. This invention also provides a method and pharmaceutical composition for treating nervous system degeneration in a mammal caused by aging or senile dementia of the Alzheimer's type, using as an active ingredient a therapeutically-effective amount of a dehydroepiandrosterone. Preferably, the dehydroepiandrosterone comprises dehydroepiandrosterone or dehydroepiandrosterone sulfate. In a preferred embodiment of this invention the compositions further comprise potassium-channel blocking amount of a potassium channel antagonist, such as 4-aminopyridine, quinine, verapamil, piracetam, or arecholine. In accordance with the present invention, dehydroepiandrosterone (DHEA) or its sulfate (DHEAS) is administered to the patient. The DHEA or DHEAS works in an as yet undefined way to facilitate the operation of the central nervous system in SDAT patients. It is believed, however, that DHEA and/or DHEAS, their intermediate metabolites, and/or androgens and estrogens synthesized therefrom under the body's own cybernetic controls, may act on special membrane receptors for them and exert a recyberneticizing effect on the cholinergic system. DHEA and DHEAS may also play coordinating roles in collagen metabolism, in general, and they may help regulate collagen deposition and removal when it is appropriate to do so. Moreover, DHEA and DHEAS are known to effect the human complement system, and, in particular, the C4 component which is essential to the smooth functioning of the complement system in its defensive role against foreign antigens. (Koo, et al., *Klin. Wochnschr,* 61, 715 (1983)). Administration of DHEA or DHEAS is believed to help restore the functioning of the human complement system, tending to normalize the increased immune response of SDAT victims. Such enhanced immune response is believed to lead to an autoimmune disorder in SDAT victims in which the central nervous system is attacked and damaged by the immune system. Finally, DHEA, DHEAS, and their biosynthetic products are believed to be involved in the normal functioning of potassium ($K^+$) channels in membranes.

In accordance with another aspect of the present invention, the DHEA and/or DHEAS administered to the SDAT patient is supplemented with a therapeutic amount of a $K^+$ channel blocker. Many of the symptoms of SDAT can be explained by the improper function of $K^+$ channels, which transport potassium through cellular membranes. It is known, for example, that general anesthetics hyperpolarize vertebrate central neurons by increasing the proportion $K^+$ channels in open configurations. The ability of the membrane of a particular cell, neural or non-neural, to metabolically integrate the chemical and physical signals which it receives and to respond in a manner reflecting their nature and intensity, be it by release of transmitter, enzyme, hormone, or antibody or by contraction or mitosis, minimally requires a critically orchestrated interaction of $K^+$ channels with the other membrane events that occur. It appears that an overabundance of $K^+$ channels in the open configuration, and the inability of the organism to modulate the $K^+$ channels, is a major cause of the loss of cyberneticization in SDAT patients. In particular, when $K^+$ channels remain open, the release of acetylcholine and neurotransmitters from activated neural elements is inhibited, decreasing neurological information transfer and rendering the organism unable to appropriately adapt and/or respond to environmental input and feedback from other neural elements.

Thus, another aspect of the present invention is the administration of a $K^+$ channel antagonist, thereby facilitating the release of acetylcholine and favoring normal information transfer between neural elements.

The present invention also includes a method for treating SDAT by administering an effective amount of DHEA or DHEAS in combination with a therapeutically effective amount of a $K^+$ channel blocker.

Moreover, the present invention includes therapeutic compositions for treatment of nervous system degeneration comprising, in combination, an effective unit-dosage amount of DHEA and/or DHEAS in combination with an effective unit dosage amount of a $K^+$ channel blocker such as 4-aminopyridine.

Also included within the scope of the present invention are such pharmaceutical preparations in a container bearing a legend directing or encouraging the use of the contents thereof for the treatment of nervous system degeneration.

Furthermore, the present invention is directed to a method for preparing a pharmaceutical composition for treatment of nervous system degeneration caused by SDAT or aging. This method includes the steps of combining a dehydroepiandrosterone with a pharmaceutically-acceptable excipient. The method also may include the formulation thereof into individual unit-dosage amounts. The method also may include the combination of the dehydroepiandrosterone with an effective amount of a potassium channel blocker such as 4-aminopyridine.

The present invention further includes a method for stimulating the growth and repair of damaged nervous system tissue, such as brain cell tissue. In one embodiment, the nervous system tissue is grown in tissue culture to which a dehydroepiandrosterone is added. Also included in this invention is a cell growth medium containing DHEA or DHEAS.

DETAILED DESCRIPTION OF PREFERRED EMBODIMENTS

Although the terms DHEA and DHEAS are used for convenience throughout this disclosure, it should be understood that the present invention includes the substitution of any dehydroepiandrosterone for DHEA. Such dehydroepiandrosterones will be understood to include prodrugs, esters, and pharmaceutically-accepted salts of DHEA.

In accordance with the present invention, the DHEA or DHEAS is administered to a patient suffering from SDAT or other, related progressive nervous-system degenerative diseases, orally, parenterally, transdermally, by intramuscular injection, or by any other accepted method for administration of pharmaceuticals. Because DHEA and DHEAS are readily absorbed in the gut, oral administration is preferred.

The $K^+$ channel antagonists to be used in the present invention may be identified, e.g., by measurement of $K_+$ uptake. Known $K^+$ channel antagonists include 4-aminopyridine, quinine, verapamil, nootropic compounds, such as piracetam, as well as arecholine. It should be emphasized that the beneficial therapeutic method of the present invention is not limited to the use of these or any other particular $K^+$ channel antagonists. Rather, the invention resides in the identification of the involvement of open $K^+$ channels in SDAT and in the use of any $K^+$ channel blocker to remedy the imbalance.

DHEA and DHEAS are non-toxic compounds having an $LD_{50}$ in mice and rats of greater than 10,000 mg/kg orally. Therapeutic dosages according to the present invention for an average, 70 kg human, range from a minimum of about 70 mg per day to a maximum of 4,000–5,000 mg/day. The preferred dosage is from about 100 mg/day to about 2,500 mg/day, and particularly preferred dosage levels are from about 200 mg/day to about 1000 mg/day.

Therapeutic dosages of the $K^+$ channel antagonists vary somewhat depending on the compound used. For example, a therapeutic dosage of 4-aminopyridine is from about 0.2 to about 4 mg/kg, and preferably from about 0.6 to about mg/kg. Effective therapeutic amounts of quinine, on the other hand, are from about 4 mg/kg to about 30 mg/kg, and preferably from about 10 to about 25 mg/kg. Equipotent amounts of other $K^+$ channel antagonists are similarly appropriate. "Equipotent" means that amount of $K^+$ channel antagonist that has the same therapeutic effect in blocking potassium channels. One suitable method for measuring $K^+$ channel antagonist activity is to measure the anticurare or muscle relaxant-reversing effect of the $K^+$ channel antagonists (using a standard muscle relaxant) in comparison to 4-aminopyridine.

The compounds of the present invention can be formulated into capsules, tablets, elixirs, and the like for oral administration. They can also be administered parenterally in liquid form in combination with a pharmaceutically-acceptable injectable carrier. Alternatively, they may be formulated into a suppository with suitable excipients, or they may be administered transdermally with a suitable penetration enhancer, such as 1-n-azacycloheptan-2-one.

In a broader sense, the present invention may be said to encompass the use of DHEA or DHEAS to prevent damage to nervous system tissue and to facilitate growth and repair of damaged nervous system tissue. Obviously, in the treatment of nervous system degeneration, the nervous system tissue (primarily brain cell tissue) is in a living organism. However, DHEA and DHEAS are very potent stimulators of the growth of nervous system tissue, such as brain cells, in culture.

When brain cells are removed from an organism, the very act of removal damages the cells in question. Separation further damages the brain cells. As shown in Example 3 that follows, DHEA and DHEAS are extremely effective in enhancing the survival of neurons in explants of brain tissue, in the outgrowth or neuritic processes from them, and in the establishment of connections between neurons. Conventional cell culture medium may include DHEA or DHEAS in concentrations of from $1 \times 10^{-3}$M to $1 \times 10^{-9}$M, and preferably from $1 \times 10^{-4}$M to $1 \times 10^{-8}$M.

The practice of the present invention can be more readily understood by reference to the following examples.

EXAMPLE 1

Four patients over 75 years old, suffering from SDAT and having well-documented, progressive SDAT symptoms, are selected. Two of the patients are given 500 mg of DHEAS three times per day for two months. The other two are given a placebo. The two patients receiving placebo exhibit no improvement, and, in fact, exhibit continuing deterioration. In contrast, the two patients receiving DHEAS show significant improvements in cognitive ability, speech, and memory. No signs of further SDAT-type deterioration are noted.

EXAMPLE 2

The experiment of Example 1 is repeated with four other SDAT patients, all over 75 years of age. In addition to 500 mg DHEAS three times daily, two patients also receive 70 mg 4-aminopyridine in combination with the DHEAS. The controls receive placebo.

After two months, the two controls show no improvement and continued deterioration. The two patients receiving DHEAS and 4-aminopyridine, on the other hand, show significant improvement in motor ability, cognition, speech, and memory. The improvement in these two patients is more pronounced than the improvement in the two patients discussed in Example 1.

EXAMPLE 3

DHEA and DHEAS in low concentrations show remarkable effects in enhancing the survival of neurons in explants of fetal mouse brain in culture, in the outgrowth of neuritic processes from them, and in the establishment of connections between neurons. Development and maturation of glial processes in the cultures also are enhanced greatly.

(a) Methods

Cultures were prepared from finely chopped, mechanically dissociated brains from 14-day old Swiss mouse embryos. Cells were plated at a density of $3 \times 10^5$ cells/cm$^2$ on poly-D-lysine coated glass cover slips and maintained at 37° C. in an atmosphere of 5% $CO_2$, 80% humidity in Dulbecco-modified ME medium supplemented with 10% fetal calf serum and containing penicillin. The medium was first changed at 5 days of culture, at which time DHEA and DHEAS was added in concentrations ranging from $10^{-4}$M to $10^{-8}$M to the experimental cultures, while the control cultures received only normal medium. The supplemented and control media were changed at 7 days and on the 9th day the cultures were fixed and immunostained by the indirect immunofluorescent method of Coons with rabbit antisera to neurofilament protein, specific for neurons, and to glial fibrillary acidic protein, which is specific for glial cells. Neuronal and glial cells identified by the above procedures subsequently will be designated as NF+ and GFAP+ cells.

Briefly, cultures were fixed by successive incubation at room temperature with 3.7% formaldehyde and 3.7% formaldehyde containing 0.2% Triton X-100, 10 min each, and incubation at 4° C. with acetone 50%, with acetone 100% and acetone 50%—2 min each. Incubation with the above-mentioned sera anti-cell markers appropriately diluted (1/20-1/30) was carried out at room temperature for 30 min.

(b) Results

In the control cultures rather sparsely distributed small NF+ neurons with short processes were observed, either isolated from each other or in clusters, consisting of a few cells. The staining was, at most, of moderate intensity. In media containing $10^{-5}$M—$10^{-8}$M DHEA, remarkable increases were found in numbers of NF+ neurons by comparison with the controls. Their processes were greatly extended, thickened, and intertwined. Numerous connections appeared to be formed between neurons and between greatly enlarged neuronal clusters, consisting of many aggregated cells. The brilliance of the fluorescence shown by the neurons and their processes was in marked contrast to the rather dull fluorescent signal observed in the controls, indicating the presence of increased contents of NF protein per unit of surface. Many of the NF+ neurons in the experimental cultures were larger than those seen in the controls. In terms of the above effects, $10^{-7}$M DHEA appeared to be the optimal concentration. Effects similar to those above were observed with DHEAS, but in the latter instance the optimal concentration was $10^{-8}$M.

Astrocytes were stained with GFAP in all cultures. In the untreated cultures, small groupings of astrocytes with short processes were noted. A remarkable increase in the presence of DHEA and DHEAS was found in the numbers of astrocytes, the extent of their fiber extension, and in brilliance of their staining, which is indicative of greatly increased amounts of GFAP per unit cell surface.

(c) Conclusion

The above results clearly suggest that DHEA can protect neurons and glial cells from the effects of injury, which in the present experiments consists in destruction of brain structure and explanation into culture dishes, and also indicate that the growth of processes by these cells and the synthesis of characteristic proteins by them may be greatly enhanced by this hormone precursor. We consider this to be cogent evidence supporting the proposed utility of DHEA in the treatment of nervous system degeneration.

Although the present invention has been described with reference to particular examples, the scope of the present invention is intended to be limited only by the claims that follow.

What is claimed is:

1. A method for facilitating the growth of brain cells, comprising the step of administering dehydroepiandrosterone or dehydroepiandroesterone sulfate to said brain cells.

2. A method as claimed in claim 1, wherein said brain cells are in tissue culture.

3. A method for promoting the growth of nervous system tissue which comprises treating said tissue with an effective amount of dehydroepiandrosterone sulfate.

4. A method as claimed in claim 3, wherein said dehydroepiandrosterone comprises dehydroepiandrosterone or dehydroepiandrosterone sulfate.

5. A method as claimed in claim 3, which further comprises simultaneously treating said tissue with an effective potassium-channel blocking amount of a potassium channel antagonist selected from the group consisting of 4-aminopyridine, quinine, verapamil, piracetam or arecholine.

6. A pharmaceutical composition for treating nervous system degeneration in a mammal caused by aging or senile dementia of the Alzheimer's type, comprising an effective amount of dehydroepiandrosterone or dehydroepiandrosterone sulfate in combination with 4-aminopyridine, quinine, verapamil, piracetam or arecholine selected from the group consisting of 4-aminopyridine, quinine, verapamil, piracetam or arecholine and a pharmaceutically-acceptable excipient.

* * * * *

UNITED STATES PATENT AND TRADEMARK OFFICE
CERTIFICATE OF CORRECTION

PATENT NO. : 4,812,447

DATED : March 14, 1989

INVENTOR(S) : Eugene Roberts

It is certified that error appears in the above-identified patent and that said Letters Patent is hereby corrected as shown below:

Column 1, line 9, insert:

--This invention was made with government support under Grant Nos. NS18858, NS18895 and RR01462 awarded by the National Institutes of Health. The government has certain rights in the invention.--

Signed and Sealed this

Second Day of March, 1993

Attest:

STEPHEN G. KUNIN

*Attesting Officer*   Acting Commissioner of Patents and Trademarks